(12) United States Patent
Lefenfeld et al.

(10) Patent No.: US 6,833,340 B2
(45) Date of Patent: Dec. 21, 2004

(54) SYSTEM FOR DELIVERY OF ACTIVE SUBSTANCES

(75) Inventors: Michael Lefenfeld, Wilmington, DE (US); Steven Berman, Cherry Hill, NJ (US); Jared Berman, New York, NY (US); Murray Katz, Woodbury, NY (US)

(73) Assignee: LB Developments, LLC, New York, NY (US)

( * ) Notice: Subject to any disclaimer, the term of this patent is extended or adjusted under 35 U.S.C. 154(b) by 0 days.

(21) Appl. No.: 10/249,555

(22) Filed: Apr. 17, 2003

(65) Prior Publication Data

US 2004/0077513 A1 Apr. 22, 2004

Related U.S. Application Data

(63) Continuation-in-part of application No. 10/248,765, filed on Feb. 14, 2003.
(60) Provisional application No. 60/319,627, filed on Oct. 18, 2002.

(51) Int. Cl.[7] .............................. C11D 3/02; C11D 3/37; C11D 3/50; A61K 9/24; A61K 9/56
(52) U.S. Cl. ....................... 510/191; 510/193; 510/441; 510/475; 424/451; 424/464; 424/475; 424/76.21; 424/76.6; 424/76.7
(58) Field of Search ................................. 510/191, 193, 510/441, 475; 424/451, 464, 475, 76.21, 76.6, 76.7

(56) References Cited

U.S. PATENT DOCUMENTS 4,522,738 A * 6/1985 Magid et al. ................. 252/90

| 4,654,341 A | 3/1987 | Nelson |
|---|---|---|
| 5,110,868 A | 5/1992 | Bellis |
| 5,307,525 A | 5/1994 | O'Brien |
| 6,462,007 B1 | 10/2002 | Pieroni et al. |
| 6,486,117 B1 | 11/2002 | Painter et al. |
| 6,555,509 B2 * | 4/2003 | Abbas et al. ............... 510/143 |

FOREIGN PATENT DOCUMENTS

| WO | WO 00149818 | 7/2001 |
|---|---|---|
| WO | WO 02056728 | 7/2002 |

* cited by examiner

*Primary Examiner*—Brian P. Mruk
(74) *Attorney, Agent, or Firm*—Nixon Peabody, LLP

(57) ABSTRACT

A method of delivery of active substances to a water-filled environment, specifically a toilet bowl, with a water-soluble polymer as the primary delivery means. The present invention is activated by placement in the water, with the soluble polymer protecting the skin from exposure to the active ingredients. The soluble polymer is composed of a bi-layer capsule or tablet, preferably, with a solid, gas, gel, or liquid core. Alkali metal particles embedded in an interior layer of the capsule or tablet react with water once an exterior layer has dissolved. The alkali metal particles elevate water temperature, especially locally to the interior layer, and volatilize active substances contained within the interior layer. The active substances are preferably deodorants. Alternatively, capsule or tablet is covered with a non-water-soluble final coating layer so that if the present invention is stored or delivered in an aqueous solution, the active substances will not be delivered until desired. The final coating layer can be breached with physical, temperature, pH changes, or otherwise as conventionally designed and available.

37 Claims, 1 Drawing Sheet

SYSTEM FOR DELIVERY OF ACTIVE SUBSTANCES

CROSS REFERENCE TO RELATED APPLICATIONS

This is a CIP application of application Ser. No. 10/248,765 filed on Feb. 14, 2003, and priority is hereby claimed to application Ser. No. 60/319627 filed on Oct. 18, 2002, as well.

BACKGROUND OF INVENTION

1. Field of the Invention

The present invention is a tablet and/or capsule, which is deposited into a toilet bowl. More specifically, it is a system of additives, colors and/or aromas for eliminating the odor, primarily, and the bacteria, secondarily, from the toilet. Additionally, the present invention has an encapsulation design used to preserve the integrity of the chemicals therein and protect the user from any tactile contact with possibly hazardous elements. The design also allows for complete transportability without the fear of contamination to the outside environment.

2. Background of the Invention

Utilizing toilets outside and inside the home are a common necessity of everyday life, despite the fact that most individuals find public toilets (i.e. restaurants, work place, dormitories, hotels) and other toilets outside the home to be foul smelling as well as dirty and discolored. In addition, when visiting family and friends, it is rather disturbing to create pungent odors in others' toilet bowls. Of course, any discoloration of a toilet bowl is also undesirable.

There are many products available on the market that a consumer may use to attempt to relieve a bad smelling toilet. Furthermore, such current solutions for deodorizing a toilet are labor intensive, bulky and not very transportable. They are generally restricted to use in a toilet that one owns. They are not feasible solutions for public toilets and/or toilets that are not under a user's direct control. While cleaners offer some deodorizing capability, such solutions might well clean a toilet, but they are incapable of preventing, masking, and/or eliminating a bad odor in the toilet and surrounding water closet as soon as the odor presents itself. Making a toilet appear clean does not necessarily result in relieving ensuing odors and/or odors that are already present.

There are tablets which will color the water in the toilet bowl, or which contain bleach or other disinfecting agents. These tablets also contain agents that are harmful to the skin, and the user must take care when handling them. Further, such tablets are typically placed in the toilet tank, as opposed to the toilet bowl. It would not be socially acceptable or practical to insert a tablet into a toilet tank not under a user's control, such as a public toilet or a toilet of family or friends. These solutions are not adaptable to the casual toilet with which the user might come into contact; and such solutions are not capable of preventing recurring odors and/or odors that are already present.

There is no invention that releases deodorants in the toilet bowl, at the water surface, and into the room at large. In addition, compared to the available products such as aerosols, stick-ups, plug in oil burners, electronic ozone deodorizers, potpourri, candles, etc., there is no invention that is easily transportable, safe, and effective. Specifically, the vast majority of deodorizers are sold in aerosol spray cans, and this limits their portability to a small segment of the population that is willing/able to go everywhere with a large purse, briefcase, knapsack, etc. and is willing to carry a bathroom spray around with them at all times. Additionally, the aerosol is typically sprayed in the room itself, and not directly in the area where the smell originates the toilet bowl. With the present invention, the odor-blocking substance is delivered in the toilet bowl at the water level the exact interface between any deposited source of objectionable odors and the air.

There is a current popular backlash concerning potential health pitfalls of atomizing sprays containing potentially toxic, polluting or noxious substances. There is a continuing backlash against the use of aerosols as being a major contributing source of environmental pollution and ozone depletion, as well as the containers being a source of trash. Many current products use quats, phenolics, naphthalene, bleach, petrochemicals such as para-dichlorobenzyne, propellants, etc., all of which are being looked at by the National Institute of Environmental Health Sciences' National Toxicology Program study as a source of carcinogens, ozone depleters, asthma initiators, and allergy triggers or catalysts. In short, a fully effective and safe product for toilet deodorizing is not currently available.

U.S. Pat. No. 5,307,525 issued to O'Brien on May 3, 1994, describes a bathroom odor eliminator dispenser that injects film forming hydrocarbon fluid into a toilet bowl. Unlike the present invention, O'Brien's device has an inlet block for receiving fluid, an outlet block for outputting fluid into the toilet bowl, and other means for moving and activating the dispenser. O'Brien's device has no means for allowing the user to carry a deodorizing agent for instantaneous discharge into a toilet bowl. O'Brien's patent is a dispenser product as opposed to the low cost, transportable, personalized delivery device of the present invention.

U.S. Pat. No. 4,654,341 issued to Nelson on Mar. 31, 1985, shows a disinfecting tablet for a toilet bowl. Nelson's tablet has an alkali metal salt of dichloroisocyanuric acid and a chloride salt selected from calcium chloride and barium chloride, where the molar ratio of alkali metal salt of dichloroisocyanuric acid to chloride salt is no greater than 4:1. Further, Nelson's tablet is essentially free of sodium carbonate/bicarbonate buffer mixtures, and it is capable of prolonged release of chlorine through metered dispensers when immersed in water. Unlike the present invention, Nelson's tablet is not designed to be carried by a user, to be held in the hand of a user, and/or to be quickly used to deodorize a toilet. Rather, Nelson's patent teaches, "the use of alkali metal salts of dichloroisocyanuric acid in tabletted toilet bowl disinfects has a major drawback in that their solubility in water is large enough so that the tablets do not have sufficient lifetime." Thus, Nelson's patent goes on to read that his tablets, "reduce the solubility of the alkali metal salt of dichloroisocyanuric acid by providing barium and calcium ions that can react with the dichloroisocyanuric acid to form either barium di(dichloroisocyanuric acid) or calcium di(dichloroisocyanuric acid). These divalent metal salts are less soluble than the alkali metal salts, and the tablet exhibits this lower solubility." Nelson's patent works with low solubility salts unlike the present invention, and deals with long time release of chemical agents into the tank as opposed to quick time deodorization in the bowl as in the present invention. Lastly, the present invention does not use alkali metal salts as a dissolution inhibitor as in Nelson's patent, but rather uses alkali metal as a catalyst for reaction.

PCT publication WO 02056728 filed by Desenna et al. and published on Jul. 25, 2002, describes a toilet bowl cleaner effervescent tablet. In short, the Desenna et al. product is a toilet bowl cleaner comprising a surfactant; and an effervescent system including an acid, wherein the effervescent system produces a significant level of foam in a toilet bowl; and wherein the cleaner has a pH from approximately 1.6 to approximately 2.2. Unlike the present invention, the Desenna et al. product is not designed to deodorize, and does not have an encapsulation designed to preserve the integrity of chemicals.

PCT publication WO 00149818 filed by Kaziska et al. and published on Jul. 12, 2001, shows an effervescent sanitizing and cleaning tablet. The ingredients include an alkaline solid of a fine powder particle size and a granular acid solid that, in the presence of water, react to generate carbon dioxide gas; a quaternary ammonium compound; and an inert filler to provide a tablet that sinks and dissolves quickly in water. Unlike the present invention, Kaziska et al.'s tablet is not designed to be carried by a user, to be held in the hand of a user, to float at the surface of the water, and/or to be quickly used to deodorize a toilet. Further, unlike the present invention, Kaziska et al.'s tablet is not designed to deodorize, and does not have an encapsulation designed to preserve the integrity of chemicals.

U.S. Pat. No. 5,110,868 issued to Bellis on May 5, 1992, describes a biodegradable composition for controlled release of chemical agents. The solid components comprise water degradable oligomers of hydroxyacetic acid and lactic acid having molecular weights of 800–4000 and containing 40–60 mole percent hydroxyacetic acid. The compositions are useful as controlled release agents for chemicals, especially as a toilet bowl cleaning component. Optional ingredients include dyes, fragrances, filler materials, surfactants, algaecides, pest control agents, quaternary ammonium salts, and mixtures thereof. Unlike the present invention, Bellis' product does not have an encapsulation designed to preserve the integrity of chemicals, but rather, the compositions of Bellis' product allow simple addition by dissolution or suspension in the polymer and are released by surface erosion of the additives. Unlike the present invention, the Bellis product deals with longevity as opposed to quick core release as in the present invention. It is a solid melt making no separate storage layers between the ingredients. Lastly, unlike the present invention, the Bellis patent utilizes its polymer to contain the active agents overtime for prolonged, controlled delivery as opposed the polymer serving as a quick release containment vessel for the active ingredients and a matrix for the highly reactive alkali metals.

U.S. Pat. No. 4,522,738 issued to Magid et al. on Jun. 11, 1985, describes a toilet bowl cleaner having an inner and outer water-soluble envelope. The inner envelope contains a basic material and the outer envelope contains both the inner envelope and an acidic material. In use, the outer envelope dissolves and releases the acidic material to clean a toilet bowl. The inner envelope then dissolves thereby releasing the basic material contained therein to neutralize the toilet bowl water, the present invention, Magid et al.'s product does not have a protective coating which immediately dissolves upon contact with water in a toilet bowl to release fragrant compounds to freshen a toilet; rather, Magid et al.'s product is designed for a two-stage release of acidic compounds followed by basic compounds and is foremost a cleansing mechanism. Moreover, Magid et al.'s product recommends "a time lapse of at least about 2 minutes between the rupture of the outer and inner envelopes." Such would not be desirable with the present invention.

U.S. Pat. No. 6,486,117 issued to Painter et al. on Nov. 26, 2002, shows a detergent tablet comprising a compressed solid body portion having at least one mold; a non-compressed, gelatinous portion mounted in the mold. The gelatinous portion has a thickening system and at least one detergent active so that the non-compressed, gelatinous portion has either a yield strength of from about 5 to about 80 Pa, or has an average viscosity of from about 100 to about 12000 cP before the non-compressed, gelatinous portion is mounted in previously mentioned mold. Painter et al.'s product is an attempt to deal with components of detergent compositions that are compressed in the tablet press. Painter et al.'s product avoids bringing detergent compositions into close proximity with one another to prevent reaction of a selected component, instability, inactivity or exhaustion of the active form of the components. Unlike the present invention, Painter et al.'s product is concerned with preventing layers of a tablet, which are subjected to more than one compression step, from being subjected to a cumulative and potentially greater overall compression pressure. Additionally, unlike the present invention, Painter et al.'s product teaches timed release as opposed to instantaneous release of compounds. Moreover, unlike the present invention, Painter et al.'s product does not teach alkali metals and their associated ions completely encapsulated within a layer to prevent premature aromatic compound delivery, such that the aromatic compound is released upon the product's contact with water.

U.S. Pat. No. 6,462,007 issued to Pieroni et al. on Oct. 8, 2002, describes a multi-layered detergent tablet having a core with a first detergent active agent; a first encapsulating layer surrounding the core, having a second detergent active agent, and an optional disruption system; a second encapsulating layer surrounding the first encapsulating layer, having a third detergent active agent and a disruption system. The disruption of the second encapsulating layer allows at least 25% of the third detergent active agent to be released prior to the release of the second detergent active agent. Pieroni et al.'s patent teaches that the core must contain a first detergent active agent but may comprise a mixture of one or more detergent active components. The first encapsulation layer must contain a second detergent active agent but may comprise a mixture of one or more detergent active components as well. Unlike the present invention, Pieroini et al.'s product must contain detergent. Also, unlike the present invention, Pieroini et al.'s product must have a disruption system and a second detergent in a first encapsulation layer. Unlike the present invention, Pieroini's et al.'s product does not teach alkali metals and their associated ions completely encapsulated within a layer to prevent premature fragrant compound delivery, such that the fragrant compound is released upon the product's contact with water.

Therefore, a need has been established for an invention that provides fast and effective deodorizing, and optionally, cleansing, and colorization to a toilet bowl where access to only the toilet bowl (as opposed to the toilet tank) is feasible and desired. Additionally, there is a need for a simple solution to toilet bowl deodorizing, and optionally cleansing and colorization that avoids the user's hands contacting harsh chemicals. There is a need for a simple solution that does not cause corrosion to specific parts of the toilet or other adverse effects on other portions of the fixtures. Furthermore, there is a need for a quick solution to removing offensive odors, and optionally discoloration and unsanitary conditions from a toilet bowl. Specifically, there is a need for removing odors remaining after a toilet bowl has been flushed with water. Moreover, there is a need for a socially acceptable method of dealing with toilet bowl smell without portraying the user as a social outcast. Also, aside from toilet tank tablets, there is a need for a simple solution to maintaining a clean scented toilet at home or away.

SUMMARY OF INVENTION

The present invention is a toilet bowl deodorizer, that is optionally a disinfectant and coloring agent, which is contained in a dissolvable casing that is non-irritating to a user's skin. The primary benefit of the present invention is to release deodorants into the bowl, at the water surface and not into the room at large. The present invention is a device and method of delivery of active substances to a water-filled environment, specifically a toilet bowl, with a water-soluble polymer as the primary delivery means. The present invention can easily be carried in a pocket for release into any toilet bowl of choice, thus, providing a quick and effective deodorizing solution. Until dropped into a toilet bowl, the present invention's chemical reactions will not occur; thus, the present invention is completely safe for storage and transport. Wrappers and other devices with similar chemically isolating properties can be used to further prevent premature reaction of the present invention.

The device is activated by contact with the water, with the water-soluble polymer protecting the user's skin from exposure to the active ingredients. The exterior layer(s) of the present invention is/are composed of water-soluble polymers, and a preferred embodiment is a bi-layer capsule or tablet. Other embodiments of the present invention have one layer or even three plus layers; the goal being to prevent outside moisture (especially human touch) from the present invention to begin a premature reaction. The desirability of a second layer stems from a recognition that alkali metals and their associated ions are completely encapsulated within the second layer itself; and thus, a second layer is part of the present invention allowing for safer user handling. The exterior polymer is a water-soluble polymer having a preferred molecular weight of, but not limited to, 100,000 to 700,000. In general, the lower the molecular weight, the faster dissolution will occur, and vice versa. The interior polymer is a water-soluble polymer having a preferred molecular weight of, but not limited to, 50,000 to 100,000. This polymer capsule contains active substances for deodorizing as well as the potential for cleaning and coloring of the toilet.

Both the exterior and interior polymer layers may have any and/or all of the following ingredients: hydrophobic polymers, sugars, glycerins, and ionic species such as salt to direct the dissolution rate of the exterior and interior polymer layers. It is contemplated that both the exterior and interior polymer layers may contain these afore mentioned ingredients; the exterior polymer layer containing between 10–30 wt. % of the total weight and the interior polymer layer containing between 5–20 wt. % of the total weight. These filler ingredients will aid in controlling the rate of the polymers' dissolution in water. The fillers assist the control being directed by the polymers' molecular weight.

The interior polymer layer and/or active layer contains alkali metals and their associated metallic ions to activate the volatility of the active ingredients. The active ingredients deodorize, and preferably also disinfect, and kill bacteria in the toilet bowl. The present invention does not harm plumbing, and is fully effective in accomplishing its goals.

In an alternative embodiment of the present invention, because all of the polymer layers of the shell, capsule, tablet, et.al., were made of a water soluble polymer containing alkali metals and other active ingredients, it has been recognized that under certain circumstances, it is desirable that the present invention be able to remain submerged in water environments for an extended period of time prior to being activated by some external force. When that force is applied, puncturing this non water-soluble outer shell, then the embodiment is once again allowed to run its water-soluble course. To accomplish this result, a final layer or layers of non-water soluble, water impermeable polymer would be applied to the exterior of the present invention.

DETAILED DESCRIPTION

Figure 1:
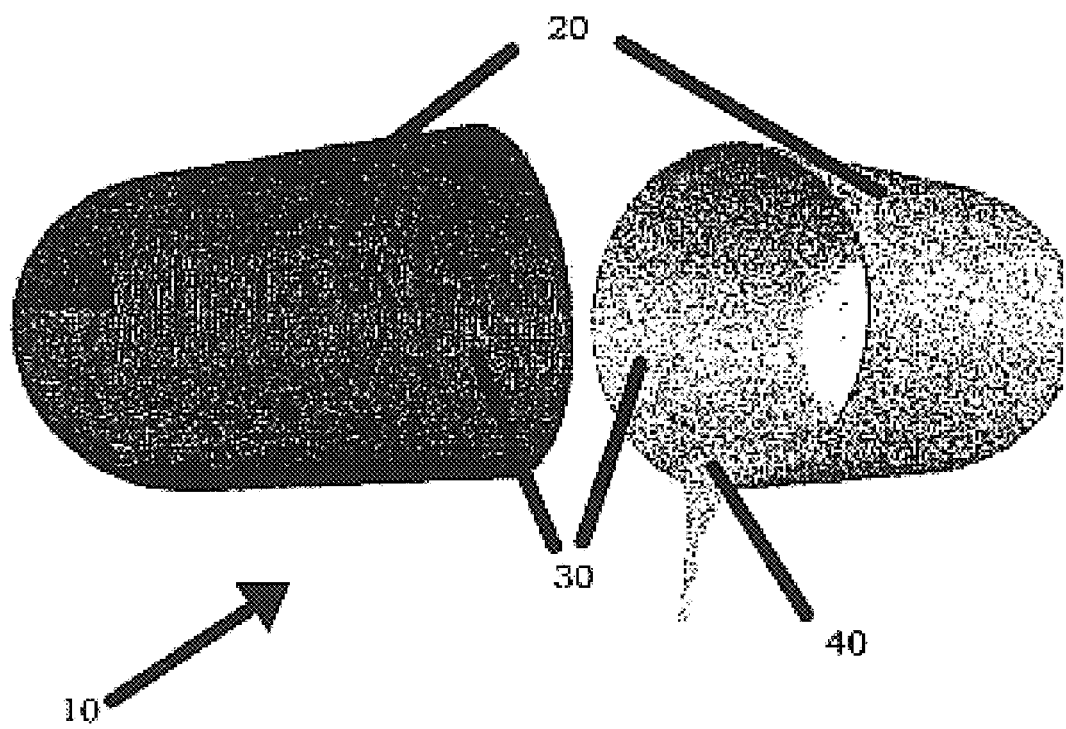
FIG. 1 shows a side view of the exterior and interior polymer layers and the active ingredients.

The present invention is a capsule or tablet device for delivery of active substances to a water-filled environment such as a toilet bowl. The capsule or tablet has an exterior polymer layer encasing an interior polymer layer, further encasing active ingredients for deodorizing, as well as, disinfecting and coloring the water. The exterior and interior polymer layers dissolve upon use and leave no particles to be retrieved by the user. Further, by using two layers of protection, the exterior polymer layer and the interior polymer layer, keeps the user from having tactile contact with the active ingredients. While the capsule can be made of one layer or multiple layers (two or more), two layers are optimal. Two layers allows for the best dissolution control, ease of production, and the safety of the product. However, additional layers may be utilized for customized applications and properties.

FIG. 1 shows a disassembled side view of the tablet or capsule (10), the exterior polymer layer (20), the interior polymer layer (30) and the active ingredients (40). The exterior polymer layer (20) is constructed of water-soluble polymers (synthetic, semi-synthetic, and natural polymers) including, but not limited to, polyvinyl alcohol polymers (PVA) and acryl amide polymers. The highly soluble exterior polymer layer (20) must dissolve quickly to expose the interior polymer layer (30), while at the same time protecting the interior polymer layer (30) prior to use. The exterior polymer layer (20) protects the user's skin from the interior polymer layer (30) and the active ingredients (40) held therein.

Each layer (20, 30) is made up of a water-soluble polymer. The solubility of the external polymer layer (20), which contains no alkali metal, is constant, and its dissolution rate dependent only upon its chemical structure, thickness and additives. Hence, in a preferred embodiment of the present invention, the thickness of the exterior polymer layer (20) will be set in manufacture to be thick enough to resist puncture, but thin enough to dissolve in seconds. Other embodiments of the present invention have an exterior polymer layer (20) with a dissolution rate of multiple minutes—as necessary to achieve delayed deodorizing (a longer dissolution rate will delay the interior polymer layer (30) from becoming exposed), to maintain increased structural integrity, and to increase susceptibility to puncture.

The preferred embodiment is an aerated exterior polymer layer (20) approaching or exceeding 500 microns in thickness, although other embodiments are possible. Some embodiments of the present invention have flavoring agents incorporated in or surrounding the external polymer layer (20). The goal is for the flavoring agents to ensure that the present invention tastes unsavory in case of accidental ingestion by a person, so that the person would be inclined to remove the present invention from inside their mouth as quickly as possible to avoid being poisoned and/or injured internally. These flavoring agents may include, but are not limited to, tannins, peppers, and alum ($KAl(SO_4)_2 \cdot 12H_2O$).

The interior polymer layer (30) which can be duplicated to provide a multiplicity of layers rather than just one—is also made of a water-soluble polymer with the addition of alkali metal and fragrance. The thickness of the interior polymer layer (30) is only that which is required to encapsulate the amount of alkali metal necessary to volatilize the fragrance. The preferred embodiment is an interior polymer layer (30) as thin as 500 microns, however thickness should ensure that the alkali metal is fully contained within the interior polymer layer (30).

If it has not heretofore been made clear, the alkali metals are, in the preferred embodiment of the present invention, contained in both the interior polymer layer (30) and as part of the active ingredients (40) in the space enclosed by the interior polymer layer (30). Alkali metals are part of the interior polymer layer (30) to locally elevate temperature for chemical reactions, faster dissolution of the polymer, and volatilization of active agents in the core. These alkali metals begin the desired reaction with the water in a toilet bowl. Alkali metals are part of the active ingredients (40) in the space enclosed by the interior polymer layer (30) as well, so that fragrances are volatized once the active ingredients (40) are exposed to the water in a toilet bowl.

The interior polymer layer (30) is pressed with alkali metals including any and or all of the following: Potassium, Sodium, Lithium, Rubidium, and/or Cesium. These alkali metal ions are important because we have determined this as the most stable method of creating an exothermic reaction with sufficient heat to volatilize the active ingredients (40) such as fragrances and cleaning actives held at the interior of the tablet or capsule (10). The reaction of each of the alkali metals yields a byproduct of an inert hydroxide and a small quantity of hydrogen gas necessary for the process to work effectively. However, any other combination of organic and inorganic chemicals that produces an exothermic reaction may be considered as well.

Based upon the alkali metals' flash point, the speed of reaction is from "slowest" to "fastest" from lithium to sodium to potassium to rubidium to cesium. The two most available alkali metals are sodium and potassium, either in their pure state or in their alloyed state. This makes them the primary economic candidates for use in the interior polymer layer (30) and active ingredients (40).

If potassium (K) is employed as one of the metals, it would be because of its availability, comparatively lower cost, volatility, flashpoint, etc. The reaction is slower than that of rubidium, but faster than that of sodium. Potassium metal reacts very rapidly with water to form a colorless solution of potassium hydroxide (KOH) and hydrogen gas ($H_2$). The resulting solution is basic because of the dissolved hydroxide. Basic chemical reactions, such as that of the present invention, which involves KOH at low concentrations, are relatively inert and non-environmentally polluting a consideration of importance since the present invention will typically empty into the environment upon being flushed in a toilet. While the by-products are caustic in nature, the amount of hydroxide generated will not reach dangerous levels in the intended quantities used or even an order of magnitude greater. At the beginning of the reaction, the potassium becomes very hot and the hydrogen off-gas catches fire and burns with a purple color.

The following equation represents the chemical reaction occurring after the exterior polymer layer (20) dissolves and exposes the alkali metal embedded within the interior polymer layer (30) to the water in the toilet bowl:$2M(s) + 2H_2O \rightarrow 2M^+(aq) + 2 OH^-(aq) + H_2(g)$; where M=alkali metal The resulting hydrogen ignites and vaporizes the deodorizers making up and contained within the active ingredients (40) in the space enclosed by the interior polymer layer (30) of the capsule or tablet (10), along with the water it is submerged in. One of the added benefits of using potassium over the other lower alkali metals is that unlike lithium and sodium, potassium produces a super-oxide ($KO_2$) when it burns in air, as shown below.

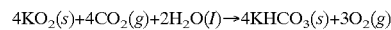
$$4KO_2(s) + 4CO_2(g) + 2H_2O(l) \rightarrow 4KHCO_3(s) + 3O_2(g)$$

This is a favorable chemical reaction that produces both the inert oxide and a surplus of oxygen. The oxide removes carbon dioxide from moist air and replaces it with oxygen. This one-off chemical process is not only desirable from an environmental standpoint, but additionally facilitates the deodorizing process. The expunged gas can be used to disperse the fragrance and increase the spread of the fragrance into the water closet environment. The expunged gas will cause disturbance in the water environment causing the water surface to agitate the fragrant oil upon it as well as heat it towards volatilization. The metal will be suspended at the water surface by the large surface area of the polymer and the core, as well as the polymers' and cores' lower density than water. This will facilitate the localized heating of the fragrance layer and allowing the off-gases to be produced to create the agitation.

If sodium (Na) is employed as one of the alkali metals, it would be because it is as comparatively low cost and as abundant as potassium. Should the speed of the reaction need to be slowed, sodium's slightly slower reaction rate and lower level of heat generation make it a candidate either in a pure form or in combination with potassium and lithium. Like potassium (discussed above), when sodium in introduced into water, it too reacts violently, forming hydrogen, which burns and creates heat, and NaOH, (commonly known as lye) which is soluble and strongly alkaline. Similar to the reaction for potassium, when sodium burns in air it also produces ionic by-products such as a crystalline chloride, (NaCl) otherwise known as common house salt, a mixture of the oxide, ($Na_2O$), and the peroxide, $Na_2O_2$. Each of these byproducts is inert, non-toxic and non-polluting and may in fact aid in the cleansing of the toilet surfaces.

If lithium (Li) is employed as one of the alkali metals, it would be primarily because the speed of the reaction needs to slowed; to be decreased slightly below that of either sodium or potassium. Lithium is less abundant than either sodium or potassium making it more costly to use. It is contemplated that slower reactions times might be desired if the fragrance and any other active ingredients (40) are to be released over a prolonged period of time. For example, the capsule or tablet (10) could be dropped into a toilet bowl before guests arrive to ensure that continuous deodorizing occurs in a bathroom and/or toilet until toilet flushing. Also, as the tablet dissolves, some instances of the alkali metals will cause the formation of a bicarbonate (e.g., Sodium Bicarbonate), which in the presence of any acidic environment (e.g. vinegar, urine, etc.) will cause the toilet water to effervesce and volatilize the fragrant layer.

If rubidium (Rb) or cesium (Cs) is employed as one of the alkali metals, it would be primarily because the speed of the reaction needs to be increased slightly above that of either lithium, sodium or potassium. Both rubidium and cesium are very rare, making them much more costly to use. Both of these alkali metals are highly volatile making them much more difficult to work with safely than the lesser reactive alkali metals. Rubidium and cesium both form hydroxides and salts in addition to hydrogen (which ignites to create heat when exposed to water), however their higher volatility makes them react even faster than potassium and generate more heat when exposed to less ambient moisture.

Care has to be exercised when handling all of the alkali metals because of their reactivity with water. Any amount of liquid water is sufficient to start the chemical reaction with the interior polymer layer (30). To prevent unintentional contact with water, such as during processing or manufacture, it may become necessary to encapsulate (i.e., microencapsulation, fluidized bed coating, etc.) the alkali metals beyond embedding them in the interior polymer layer (30). Other than their combustibility, alkali metals by themselves are not toxic to man and do not present a hazard to the environment since they are among the most prevalent elements, by weight, found on the Earth.

Regardless of the combination of the possible alkali metals in the interior polymer layer (30), when the exterior polymer layer (20) dissolves and contact is made between the water and the alkali metals embedded in the interior polymer layer (30), an exothermic reaction will occur and liberate and ignite a highly flammable hydrogen gas. The resultant heat from the exothermic reaction quickens the polymer dissolution and volatilizes the active ingredients (40) at the core of the capsule or tablet (10), releasing the active ingredients (40) into the water of the toilet bowl.

The active ingredients (40) in the core of the capsule or tablet (10) include, but are not limited to, water-soluble polymers, surfactants, fragrances and cleaning agents. The core can be solid, gas, gel, or liquid in nature. If the core of the capsule or tablet (10) is a solid, it has a matrix of water-soluble polymers, fragrances, and cleaning agents. The solid core will need to be water-free. Heat drying may be used, however other methods of drying include azeotroping with benzene or loading the polymer with magnesium sulfate, Drierite, alum and/or molecular sieves. Once the core of active ingredients (40) is dry, water sensitive solid components can be added to the system. These additives will include both metal ions and any number and variety of cleaners. The core can either be pressed into the outer polymer encasing or the polymer can be rolled around the core. If the core of the active ingredients (40) is a liquid, a gel, or a gas, standard and conventional manufacturing techniques will be applied.

The active ingredients (40) are divided into four main categories: fragrances, disinfectants, surfactants, and colors or dyes. The fragrances can include any and or all of the following types of ingredients: aromatics, essential oils, aromatic chemicals, and/or terpenes. The disinfectants can include any and/or all of the following ingredients; chlorine based cleansers, peroxide phenols, dibutylphthalates (DBPs), alcohols, aldehyde, quaternary ammonium compounds, phenolic compounds, and/or idophor. The surfactants can include anionic/nonionic blends, sulfates, cocamides, oxides, sulfonates, ethoxylates, phosphates, acids, alkanolamides (amides), and esters. The colors and or dyes can include any and/or all of the following ingredients: organic pigments, alcohol base dispersions, water base dispersions, oil base dispersions, fluorescent dyes and pigments, solvent dyes, natural dyes, food colors, acid dyes, and/or basic dyes.

By creating a multi-layer capsule or tablet (10) consisting of polymer and fragrance contained within a layer of polymer and alkali metal, the present invention can selectively distribute substances depending upon reactions; thus, various embodiments of the present invention are created. Each metal with highest reaction temperature would be placed closer to the outside. For example, potassium would be encapsulated in the outer layer to induce quick and high temperature heating, which in turn will liberate the inner layers in which sodium and lithium would be contained. The sodium and lithium would thereby volatilize the active ingredients, namely fragrance, cleaners, et.al. This would cause the water to heat up quickly and cause the polymer to dissolve more quickly, which would therefore expose the next layer of metal and polymer faster to vaporize the fragrance. While the number of layers of in the capsule or tablet (10) can be infinite, the actual number is a finite number.

It is the outermost layer's dissolution rate that will be most effected by the temperature of the water in the toilet bowl. The colder the toilet bowl water, the slower the dissolution rate of the polymer. Conversely, the warmer the water in the toilet bowl, the faster the dissolution rate will be. However, the polymer used in the outermost layer can and will be adjusted according to, any extremes through conventional variations to control dissolution speed. The temperature of the toilet bowl water does not affect the inner components, though, since the alkali metal will determine the localized temperature because heat is generated through the alkali metal's reaction. Research indicates that anything else in the toilet bowl, other than a flammable liquid, will have no ill effect on the reactions of the present invention. In general, it is the vapors given off at the surface of the toilet bowl water by volatile flammable liquids that burn, and it is these vapors that can be ignited by sufficient amounts of alkali metals. However, should there be large amounts of alcohol in the toilet bowl, the rate of reaction of the present invention is inversely proportional to the molecular weight of the alkyl alcohol. It is believed that the rate of reaction trend begins to deviate at butanol or pentanol. The more acidic the hydrogen of the alcohol, the faster the reaction occurs. So, lower molecular weight primary alcohols react rapidly with all of the alkali metals, the heavier of the metals (K, Rb and Cs) reacting rapidly enough to ignite if exposed to air. The alcohol in question would derive from cleaners, disinfectants or other sources poured directly into the toilet bowl. Any adverse reaction of alkali metals to oils is minimal, if not miniscule, since these metals are commonly stored in oil. Ammonia ($NH_3$) is normally not considered an acidic material, but alkali metals in high concentrations are such strong bases that they liberate hydrogen from even ammonia. This will speed up the vaporization due to a conceivable increase in available hydrogen. While the concentrations of both ammonia and alkali metal would far exceed those available in normal usage, and the availability of alkali metal would have to well exceed the amounts in the tablet or capsule (10), a note of caution needs to be made. Therefore, even if there is more hydrogen, there is no real danger unless there is a great deal of alkali metal present, far exceeding the amount of metal within the present invention.

Irrespective of the toilet bowl size or whether the bowl is of the older (i.e., more water in the bowl) or newer (i.e., less water in the bowl) type, the water volumes are inconsequential, and therefore should not affect the effectiveness of the present invention. The amount of active ingredients (40) is not geared to the amount of water in a toilet bowl, but rather to the size of the bathroom needing to be deodorized. The capsule or tablet (10) can be manufactured of various sizes so that an appropriately sized capsule or tablet (10) is available for a range of bathroom volumes. In the preferred embodiment, the size of the tablet or capsule (10) is small enough for carrying convenience, but bigger than medication size tablet and caplet.

Normal operational procedure is for the tablet or capsule (10) to be added to a water-filled, unused toilet bowl, either before use or after flushing. If however, there is toilet tissue or fecal matter in the toilet bowl when the tablet or capsule (10) is deposited, so long as the toilet tissue or fecal matter does not obstruct contact with the water (an unlikely scenario) than it will have no adverse effect on the efficiency of the tablet or capsule (10). There is little fear of igniting the toilet tissue since it will already be saturated with water.

The shape and size of the capsule or tablet (10) is irrelevant and limited only by imagination. However, shapes with greater surface areas with high surface area to volume ratios and with corners (corners will provide more micro cracks for water to penetrate) will offer a slight advantage in the rate of dissolution of the tablet or capsule (10).

Time released components (fragrance) can be encapsulated using natural polymers and placed in the core of active ingredients (40) with freely flowing deodorizing components. Should there be any active ingredients (40) incorporated into the design that interact poorly with other active ingredients (40), we encapsulate such poorly interacting active ingredients (40) using water-soluble polymers as well, so that the different active ingredients (40) do not pose interaction problems.

Humidity and perspiration will have minimal effect on the tablet or capsule's (10) dissolution; however, it is possible that someone with wet hands might present a problem handling the tablet or capsule (10). This can be controlled either by increasing the exterior polymer layer (20) thickness or through packaging of the present invention. A great deal of attention is paid to packaging the tablet or capsule (10). Individual wrappers, which are water-soluble themselves (i.e. rice paper), are one embodiment. Another embodiment of the present invention has individually dispensed packets such as those presently used for chewing gum.

Various embodiments of the present invention may contain the following: a fizzing agent added to the active ingredients (40) to give a visual sensation of the present invention working (this will also increase the efficiency of releasing the fragrance into the air, although the metal-oxide formation will already give this visual sensation regardless of the fizzing agent); a color-changing agent that begins at one color, but once activation of the active ingredients (40) is complete, the color changes to another color; various fragrances and colors formulating the active ingredients (40).

An alternative embodiment of the present invention recognizes that a final coating layer (not shown) is required to enhance the tablet or capsule (10). It is oftentimes the case that there are stability issues incommercialin use, and providing a final coating layer exterior of the external polymer layer (20) will maintain the present invention's reaction ability. There is therefore a distinct need for a means to separate the active ingredients (40), as well as the external polymer layer (20) and internal polymer layer (30) up until the final moments before their intended use. Complicating matters is that when the active ingredients (40) are combined, an activation energy is most often also needed to produce a desired endpoint. Hence, the benefit of use of this alternative embodiment that will provide the heat energy needed for the reaction, only once exposed to the aqueous environment.

Another way to look at this alternative embodiment is to recognize that most of the commonly used commercial products are based on an aqueous formulation, and that a package for the separation of these active ingredients must be created to withstand diffusion of water. This is accomplished by coating the tablet or capsule (10) with final coating of various water impermeable polymers, such as (but not limited to) polyethylene, polypropylene, styrenic block copolymers (Kraton), Noryl Poly (2,6-dimethyl-1,4-phenylene oxide) (PPO), various modified polyphenylene oxide and polyphenylene ethers, and Polyetheretherketone (PEEK).These polymers are all commonly known polymers and are often used as sealants. The polymers listed above are just samples of the types of polymers that can be used to seal the tablet or capsule (10). All of these polymers can be applied in hot melt form and retain excellent flexural and tensile properties. Any and all conventional methods of applying the polymers to the tablet or capsule (10) can be employed the key being that the final coating layer is exterior of the exterior polymer layer (20). The final coating layer is breached when any conventional method of physically applying pressure to break the final coating layer is performed. In addition, or alternatively, the final coating layer is breached upon a pH change, temperature change, or any other change. The mechanism for the breach of the final coating layer is any conventional method that allows for breach in response to the appropriate circumstance. The present invention is not limited to the sole embodiments described above, but encompasses any and all of the embodiments in the following claims.

We claim:

1. An active substance delivery system, comprising:
   at least one active ingredient;
   an alkali metal in its neutral state;
   a first water-soluble polymer interior layer, surrounding said active ingredient and said alkali metal; and
   a water-soluble polymer exterior layer, surrounding said water-soluble polymer interior layer.

2. An active substance delivery system of claim 1, wherein said water-soluble polymer exterior layer comprises a polyvinyl alcohol polymer or an acryl amide polymer.

3. An active substance delivery system of claim 1, wherein said at least one active ingredient is selected from a deodorant, a cleanser, a disinfectant, a colorant or dye, a water-soluble polymer, a surfactant, a fizzing agent, and mixtures thereof.

4. An active substance delivery system of claim 3, wherein said at least one active substance is selected from a deodorant, a colorant or dye, a disinfectant, a fizzing agent, and mixtures thereof.

5. An active delivery system of claim 3 in the form of a capsule.

6. An active delivery system of claim 3 in the form of a tablet.

7. An active substance delivezy system of claim 3, wherein at least a portion of said alkali metal is encapsulated within said first water-soluble polymer interior layer.

8. An active substance delivery system of claim 7, wherein said alkali metal is fully contained within said first water-soluble polymer interior layer.

9. An active substance delivery system of claim 3, further comprising at least a second water-soluble polymer interior layer, surrounding first water-soluble polymer layer.

10. An active substance delivery system of claim 9, wherein at least a portion of said alkali metal is encapsulated within said first water-soluble polymer interior layer or said second water-soluble polymer interior layer.

11. An active substance delivery system of claim 1, wherein said alkali metal is encapsulated.

12. An active substance delivery system of claim 1, wherein said alkali metal is selected from lithium, rubidium, and cesium.

13. An active substance delivery system of claim 1, wherein said alkali metal is selected from sodium and potassium.

14. An active substance delivery system of claim 13, wherein said at least one active ingredient is selected from a deodorant, a cleanser, a disinfectant, a colorant or dye, a water-soluble polymer, a surfactant, a fizzing agent, and mixtures thereof.

15. An active substance delivery system of claim 14, wherein said at least one active substance is selected from a deodorant, a colorant or dye, a fizzing agent, and mixtures thereof.

16. An active substance delivery system of claim 14, wherein said alkali metal is encapsulated.

17. An active delivery system of claim 14 in the form of a capsule.

18. An active delivery system of claim 14 in the form of a tablet.

19. An active substance delivery system of claim 13, wherein at least a portion of said alkali metal is encapsulated within said first water-soluble polymer interior layer.

20. An active substance delivery system of claim 13, wherein said alkali metal is fully contained within said first water-soluble polymer interior layer.

21. An active substance delivery system of claim 20, further comprising at least a second water-soluble polymer interior layer, surrounding first water-soluble polymer interior layer.

22. An active substance delivery system of claim 21, wherein at least a portion of said alkali metal is encapsulated within said first water-soluble polymer interior layer or said second water-soluble polymer interior layer.

23. An active substance delivery system of claim 13, wherein said at least one active substance is selected from a deodorant, a disinfectant, a colorant or dye, a fizzing agent, and mixtures thereof, and said alkali metal is sodium.

24. An active substance delivety system of claim 13, wherein said at least one active substance is selected from a deodorant, a disinfectant, a colorant or dye, a fizzing agent, and mixtures thereof, and said alkali metal is potassium.

25. A method for delivering an active substance to an aqueous system, comprising the step of:

contacting an aqueous system with an active substance delivery system of claim 1.

26. A method for deliveiing an active substance to an aqueous system, comprising the step of:

contacting an aqueous system with an active substance delivery system of claim 3.

27. A method for delivering an active substance to an aqueous system, comprising the step of:

contacting an aqueous system with an active substance delivery system of claim 13.

28. A method for deliveang an active substance to an aqueous system, comprising the step of:

contacting an aqueous system with an active substance delivery system of claim 23.

29. A method for delivering an active substance to an aqueous system, comprising the step of:

contacting an aqueous system with an active substance delivery system of claim 24.

30. A method for deodorizing toilet waters, comprising the step of:

contacting toilet water with an active substance delivery system of claim 4.

31. A method for deodorizing toilet waters, comprising the step of:

contacting toilet water with an active substance delivery system of claim 15.

32. A method for deodorizing toilet waters, comprising the step of:

contacting toilet water with an active substance delivery system of claim 23.

33. A method for deodorizing toilet waters, comprising the step of:

contacting toilet water with an active substance delivery system of claim 24.

34. An active substance delivery system of claim 1, wherein said first water-soluble polymer interior layer has a molecular weight of 50,000 to 100,000.

35. An active substance delivery system of claim 1, wherein said water-soluble polymer exterior layer has a molecular weight of 100,000 to 700,000.

36. An active substance delivery system of claim 13, wherein said first water-soluble polymer interior layer has a molecular weight of 50,000 to 100,000.

37. An active substance delivery system of claim 13, wherein said water-soluble polymer exterior layer has a molecular weight of 100,000 to 700,000.

* * * * *